(12) United States Patent
Park et al.

(10) Patent No.: US 11,311,270 B2
(45) Date of Patent: Apr. 26, 2022

(54) INTERVOLUME LESION DETECTION AND IMAGE PREPARATION

(71) Applicant: Siemens Healthcare GmbH, Erlangen (DE)

(72) Inventors: Jin-hyeong Park, Princeton, NJ (US); Michal Sofka, Princeton, NJ (US); Shaohua Kevin Zhou, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 948 days.

(21) Appl. No.: 15/579,999

(22) PCT Filed: Jul. 2, 2015

(86) PCT No.: PCT/US2015/038931
§ 371 (c)(1),
(2) Date: Dec. 6, 2017

(87) PCT Pub. No.: WO2017/003480
PCT Pub. Date: Jan. 5, 2017

(65) Prior Publication Data
US 2018/0168536 A1    Jun. 21, 2018

(51) Int. Cl.
*A61B 8/00* (2006.01)
*A61B 8/08* (2006.01)
*G06T 7/73* (2017.01)

(52) U.S. Cl.
CPC ............ *A61B 8/0825* (2013.01); *A61B 8/085* (2013.01); *A61B 8/4461* (2013.01); *A61B 8/483* (2013.01); *A61B 8/488* (2013.01); *A61B 8/5207* (2013.01); *A61B 8/5253* (2013.01); *G06T 7/73* (2017.01); *A61B 8/523* (2013.01);
(Continued)

(58) Field of Classification Search
CPC ...... A61B 8/0825; A61B 8/5253; A61B 8/085
See application file for complete search history.

(56) References Cited

U.S. PATENT DOCUMENTS 4,455,872 A * 6/1984 Kossoff ............... A61B 8/0825
128/915
2005/0232474 A1 * 10/2005 Wei .......................... G06T 7/11
382/128
(Continued)

FOREIGN PATENT DOCUMENTS

CN   101473349 A      7/2009
WO   WO2014150578 A1  9/2014
WO   WO2014162232 A1  10/2014

OTHER PUBLICATIONS

International Search Report dated Mar. 23, 2016 in corresponding International Application No. PCT/US2015/038931.
(Continued)

*Primary Examiner* — Rajeev P Siripurapu

(57) ABSTRACT

An anatomical structure is detected (110) in a volume of ultrasound data by identifying (150) the anatomical structure in another volume of ultrasound data and generating (155) an image of the anatomical structure and an anatomical landmark. A group of images are generated (130) of the original volume and compared (140) to the image of the other volume. An image of the group of images is selected (150) as including the anatomical structure based on the comparison.

18 Claims, 7 Drawing Sheets

(52) U.S. Cl.
CPC .................... *G06T 2200/04* (2013.01); *G06T 2207/10136* (2013.01); *G06T 2207/30068* (2013.01)

(56) References Cited

U.S. PATENT DOCUMENTS

| | | | |
|---|---|---|---|
| 2006/0110022 A1* | 5/2006 | Zhang | G06T 5/40 |
| | | | 382/132 |
| 2009/0076385 A1* | 3/2009 | Jackson | A61B 8/0825 |
| | | | 600/437 |
| 2009/0149756 A1 | 6/2009 | Soler et al. | |
| 2013/0035596 A1 | 2/2013 | Ionasec et al. | |
| 2014/0364726 A1 | 12/2014 | Pagoulatos et al. | |
| 2015/0133784 A1 | 5/2015 | Kapoor et al. | |
| 2015/0157298 A1 | 6/2015 | Park et al. | |

OTHER PUBLICATIONS

Ijaz, Umer Zeeshan, et al. "Optimization strategies for ultrasound vol. registration." Measurement Science and Technology 21.8 (2010): 085803.

Chinese Office Action dated Mar. 30, 2020 in corresponding Chinese Patent Application No. 201580082801.X.

\* cited by examiner

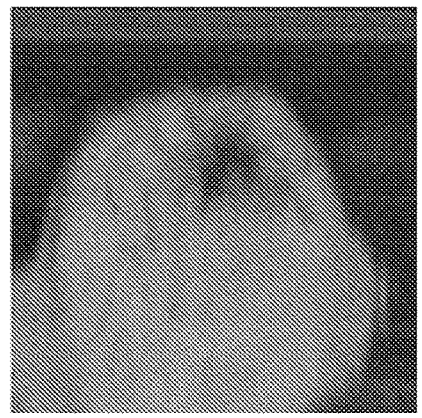
FIG. 5B
 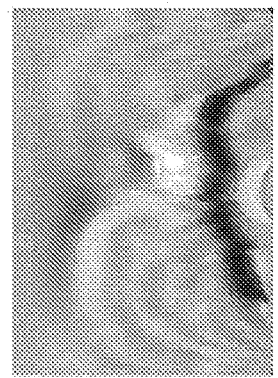 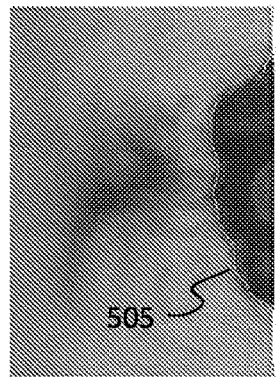
FIG. 5C　　　　　　　　FIG. 5D　　　　　　　　FIG. 5E

INTERVOLUME LESION DETECTION AND IMAGE PREPARATION

CROSS-REFERENCE TO RELATED APPLICATIONS

This application is a national phase filing under 35 U.S.C. § 371 of International Patent Application No. PCT/US2015/038931, filed Jul. 2, 2015, which is incorporated herein by reference in its entirety.

BACKGROUND

Volumetric ultrasound is used to image a patient, such as imaging patient breasts to detect and/or display lesions. Multiple volumes may be required to fully image the breast. These multiple volumes may include overlapping regions of the patient. Lesions or other anatomical structures may be present in multiple volumes. However, the volumes are acquired from different angles or perspectives, so the position of particular lesions relative to the different volumes may vary. This position variation between volumes may make it difficult to track or locate a particular lesion across the different volumes.

BRIEF SUMMARY

By way of introduction, the preferred embodiments described below include methods and systems for ultrasound imaging. An anatomical structure represented by ultrasound data is identified in a volume, and an image is generated from the ultrasound data that includes the anatomical structure. Images are generated from ultrasound data of a different volume, and the series of images are compared to the other image to determine the existence of the anatomical structure in the different volume.

In a first aspect, a method of detecting an anatomical structure in a first volume of ultrasound data involves detecting the anatomical structure in a second volume of ultrasound data, the second volume and the first volume representing different but overlapping regions of a patient. The method also involves generating, by a processor, a second image of a second slice of the second volume, the second slice comprising data representing a plane in the second volume and including the anatomical structure and an anatomical landmark. The method also involves generating, by the processor, a series of images of slices of the first volume, the slices of the first volume comprising data representing planes in the first volume and including the anatomical landmark. The method also involves comparing, by the processor, the series of images to the second image, and identifying, by the processor based on the comparing, a first image from the series of images that contains a representation of the anatomical structure.

In a second aspect, a system for detecting an anatomical structure in a first volume of ultrasound data involves at least one memory operable to store a first and a second volume of ultrasound data, the ultrasound data representing different but overlapping regions of a patient. The system also involves a processor configured to detect the anatomical structure in a second volume of ultrasound data, generate a second image of a second slice of the second volume, the second slice comprising data representing a plane in the second volume and including the anatomical structure and an anatomical landmark, generate a series of images of slices of the first volume, the slices of the first volume comprising data representing planes in the first volume and including the anatomical landmark, compare the series of images to the second image, and identify, based on the comparison, a first image from the series of images that contains a representation of the anatomical structure.

In a third aspect, a non-transitory computer readable storage medium having stored therein data representing instructions executable by a programmed processor for detecting an anatomical structure in a first volume of ultrasound data. The storage medium contains instructions to detect the anatomical structure in a second volume of ultrasound data, the second volume and the first volume representing different but overlapping regions of a patient. The storage medium also contains instructions to generate a second image of a second slice of the second volume, the second slice comprising data representing a plane in the second volume and including the anatomical structure and an anatomical landmark. The storage medium also contains instructions to generate a series of images of slices of the first volume, the slices of the first volume comprising data representing planes in the first volume and including the anatomical landmark. The storage medium also contains instructions to compare the series of images to the second image, and identify based on the comparing, a first image from the series of images that contains a representation of the anatomical structure.

The present embodiments are defined by the following claims, and nothing in this section should be taken as a limitation on those claims. Any one or combinations of any two or more of the aspects discussed above may be used. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIGS. 5A-E illustrate example ultrasound image processing.

DETAILED DESCRIPTION OF THE PREFERRED EMBODIMENTS

A lesion, or other anatomical structure, may be detected in an initial volume of ultrasound data representing a region of a patient, such as a volumetric breast scan of the patient. An image of the lesion may be derived from the initial volume. This image may then be compared to other images derived from other ultrasound volumes of the region of the patient, with this comparison yielding an identification of the lesion in the other ultrasound volumes.

Volumetric scans may provide comprehensive data for lesion analysis since such scans are able to capture data representing a whole breast in three dimensions. Multiple overlapping volumetric scans may be needed to achieve this full representation. As such, lesions in the breast may be represented by data of multiple volumetric scans. These multiple scans may each provide different views or perspectives of the lesion.

Identifying a particular lesion across multiple scans may be achieved through first identifying the particular lesion in a first volumetric data. This detection may be achieved through the use of a fully automatic lesion segmentation algorithm, semi-automatic, or manually to determine the lesion boundaries in the first volumetric data. Next, the lesion data of the first volumetric data may be used to locate the lesion in other volumetric data.

In an embodiment, a two dimensional (2D) breast detection algorithm is applied to each slice of a first volume. Then, an anatomical landmark, such as a nipple, is detected using a three dimensional (3D) landmark detection algorithm. A 2D slice of the first volume that includes both the anatomical landmark and the lesion is selected by rotating planes centered at the nipple and oriented relative (e.g., perpendicularly) to a current view. An image for the selected slice is generated. In a second volume, images are generated using a plane. The plane is moved or rotated to generate the different images, such as orienting the plane perpendicular to a current view that contains the nipple and the lesion of interest segmented in the first volume. The images of the second volume are compared to the image of the first volume, with the best matching image (e.g. highest matching score) being determined to be an image containing the lesion. Measurements of the location and characteristics of the lesion may be determined from the matching image and/or correlated back to the second volume for further analysis.

Breast imaging is used in the examples herein. In other embodiments, the anatomical structure detection is used for scanning other parts of the patient. Abdominal, small organ, and peripheral vascular are some other examples.

Figure 1:
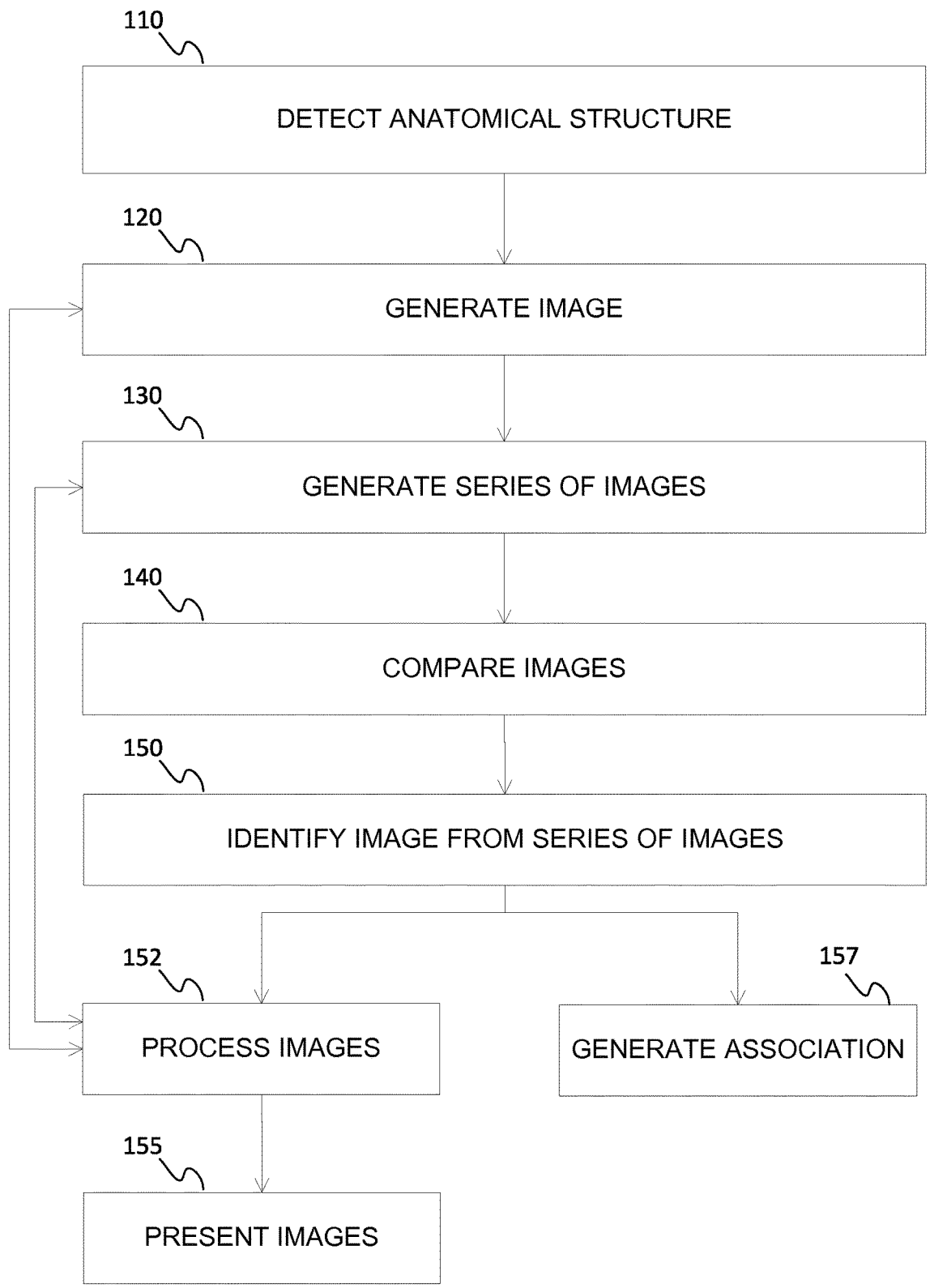
FIG. 1 a flow chart diagram of one embodiment of a method for ultrasound imaging for anatomical structure detection.

FIG. 1 is a flow chart diagram of one embodiment of a method for anatomical structure detection in medical diagnostic ultrasound volume imaging. The method may be implemented by the system, processor, and/or computer readable media shown in FIG. 4, but other systems may be used. For example, multiple computerized systems may interact and/or communicate to implement the method, such as an imaging system interacting with a computer or server.

Additional, different, or fewer acts may be performed. For example, acts 155 and/or 157 may not be performed. The method is performed in the order shown or another order. For example, act 152 may be performed after act 120 and prior to act 130.

In act 110, an anatomical structure is detected. The anatomical structure may be detected in a second volume, as differentiated from a first volume. The second and the first volume may represent different but overlapping regions of the patient. First and second are may or may not represent an order of acquisition.

Any anatomical structure is detected, such as a lesion, other irregular structure, nipple, other regular structure, or any other anatomy. In other embodiments, an inserted device is detected.

The anatomical structure may be detected using any technique. For example, 3D volumetric segmenting techniques may be used. Also, in an embodiment, successive parallel planes are selected through the second volume, thus representing 2D planes of the 3D volume. The 2D planes, or images generated therefrom, may be analyzed and/or segmented, for example using edge detection techniques, to detect the anatomical structure. For example, pixel intensity differentiation or edge detection may be used. In an embodiment, a user manually selects the anatomical structure from the volume using a user input device, such as a keyboard or touchscreen display.

In act 120, an image is generated. A generated image may or may not be displayed. Image as used herein may be a frame of data that may be processed to produce an image, so may or may not include RGB display values.

The image may be of a 2D slice of the second volume. The slice involves data representing the plane, thus the image is an image of the plane. The slice corresponds to a slice generated by scanning or is a slice with an arbitrary orientation relative to the scanned volume.

The slice and the image include data representing the anatomical structure as well as data representing an anatomical landmark. The anatomical landmark may be any known and detectable anatomical portion of a patient, such as a nipple on a breast being scanned. In an embodiment, generating the image involves generating the image with the anatomical landmark in a center of the image.

The landmark is determined manually. The user designates the location of the landmark on one or more images. Alternatively, a processor locates the landmark using filtering, classification, or other automatic process. Semi-automatic identification of the landmark may be used. The same landmark points are identified in different volumes. For example, a nipple is located in the volumes, and the nipple locations are then used as anchor points to align or register the images generated from the volumes.

In act 130, a series of images is generated. The series of images may be of the first volume, as distinguished from the image generated of the second volume in act 120. The series of images of are of slices of the first volume. The slices of the first volume involve data representing planes in the first volume and including the anatomical landmark, such as a nipple as described above. The landmark is detected in the various volumes using a same or different approach (e.g., manual, automatic, or semi-automatic).

Figure 3A:
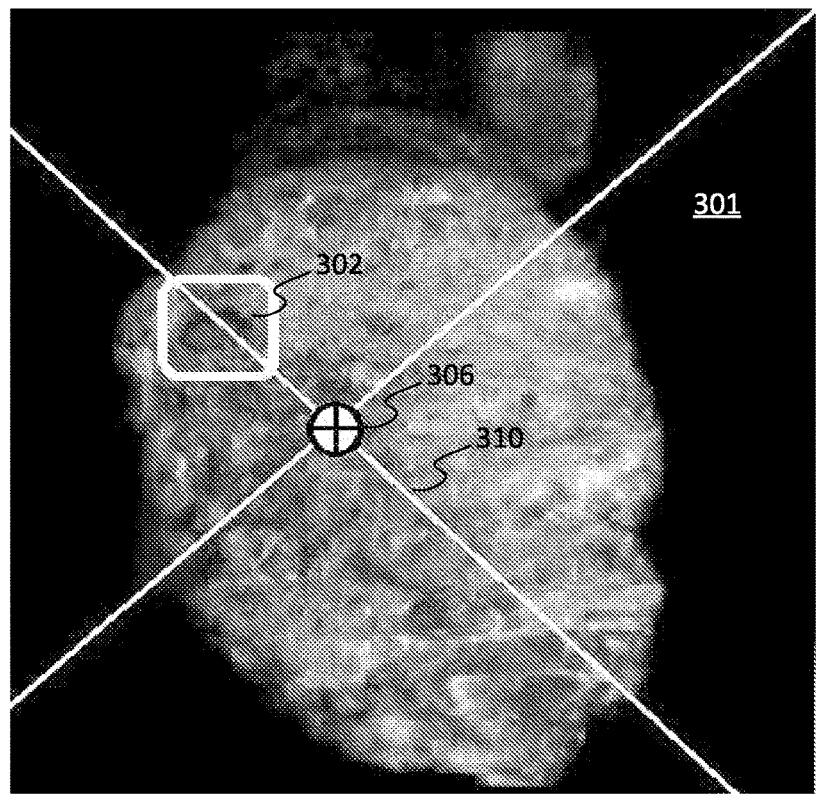
FIGS. 3A-D illustrate example anatomical structure detection.
Figure 3B:
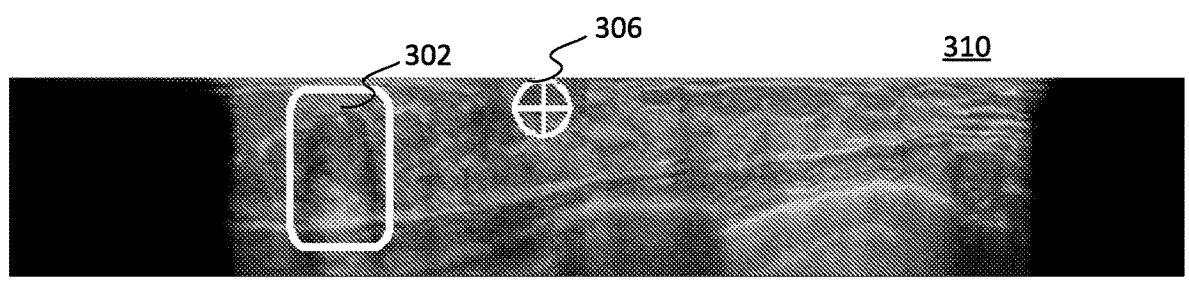
Figure 3C:
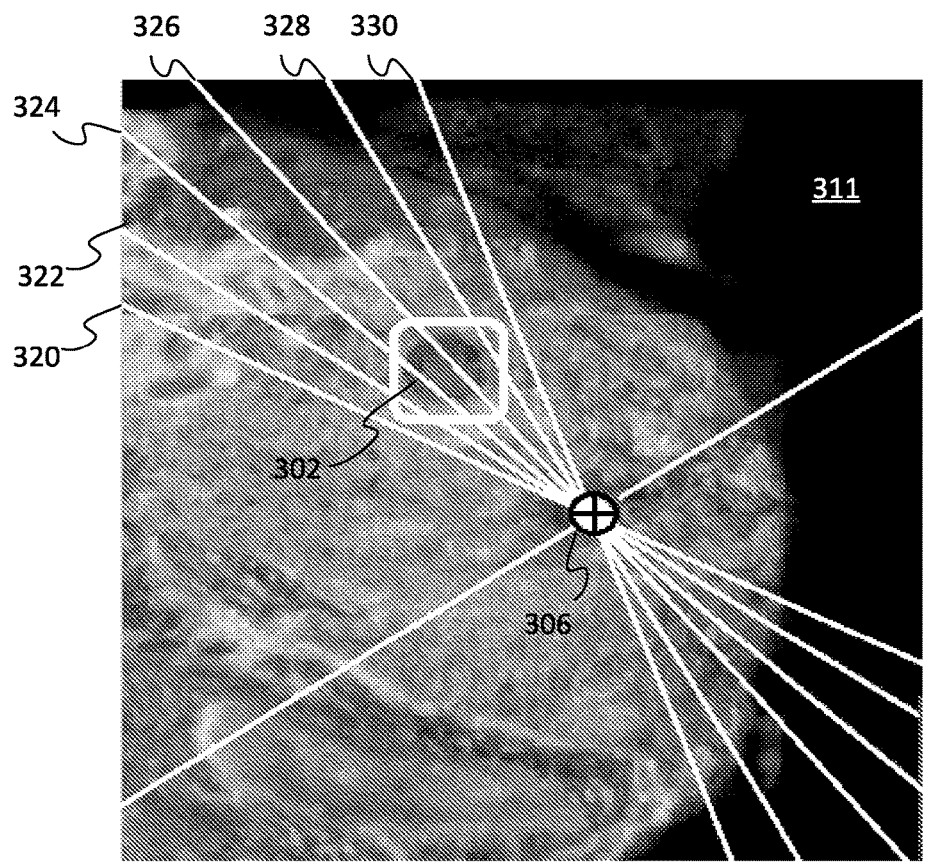

In an embodiment, images for slices of the first volume are incrementally generated in a radial pattern having the anatomical landmark as the origin, such as is illustrated with respect to FIG. 3C. In this embodiment, the radial pattern may include slices of the first volume selected for a predetermined range of angles, such as from zero degrees to 180 degrees based on a selected origin line intersecting the anatomical landmark. The line is an axis about which the plane is positioned in various orientations as shown in FIG. 3. In an embodiment, generating the series of images involves generating the images with the anatomical landmark in a center of the image. Other orientations and/or positions for the planes may be used, such as a stack of slices intersecting a sub-volume defined by the landmark.

In act 140, images are compared. The image of the second volume may be compared with the series of images of the first volume. In an embodiment, images with the anatomical landmark at the center of the image are compared. Other images may be compared.

In act 150, an image is identified from the series of images. The identified image is identified based on the comparison of act 140. The identified image contains a representation of the anatomical structure. Since the image from the second volume is selected to include both the landmark and the anatomical structure, the identified image from the series may be selected based on also including both the landmark and the structure.

The image may be identified using any technique. For example, similarity measures and/or scoring may be used. Techniques such as structural similarity index (SSIM), peak signal-to-noise ratio (PNSR), minimum sum of absolute differences, correlation, and/or mean squared error (MSE) may be used. In an embodiment, the identified image is an image that has a highest, or best, similarity score. The reference image from the second volume includes both the landmark and the structure. By identifying the image from the series generated from the first volume as the most similar, this identified image more likely includes both the landmark and the structure.

In act 152, images are processed. The images may be processed to refine and/or improve the image. In an embodiment, an outline of a body part of the patient is established in an image, and ultrasound representations of matter outside the outline in the image are removed. For example, images are refined through patient body part silhouette determination to remove representations of ultrasonic gels or other materials from the image, as is described with respect to FIGS. 2 and 5A-5E. The images may be processed prior to display or presentation, such as in act 155, or at other times, such as after act 120 and/or act 130. In such an embodiment, the comparison of act 140 occurs between processed images. For example, comparing the series of images to the image of act 120 involves comparing the image and the series of images after the removing and/or any segmentation.

In act 155, images are presented. The presented images are the image from the first volume and/or the identified image from the second volume, each of which contains a representation of the anatomical structure and the anatomical landmark. The images may be shown at the same time, or at different times. The images may be shown on a display, such as the display 24 described with respect to FIG. 4.

In act 157, an association is generated. The association links the structure and/or landmark in the reference image and the identified image. For example, the lesion in both images is linked to indicate the same lesion from the different perspectives or for the different volumes.

The association may be an association or other associative reference specifically indicated in a record of a database. The database may be contained in, or accessible by, an electronic medical record system, a computer computerized physician order entry (CPOE) system, an automated workflow system, a review station, a workstation, a computer, a picture archiving and communication system (PACS) station, a server, combinations thereof, or other information technology system in or associated with a medical facility, practitioner, care giver, and/or patient. In an embodiment, the anatomical structure is provided an identifier, such as an index number or code, and this code is stored in association with both images.

Figure 2:
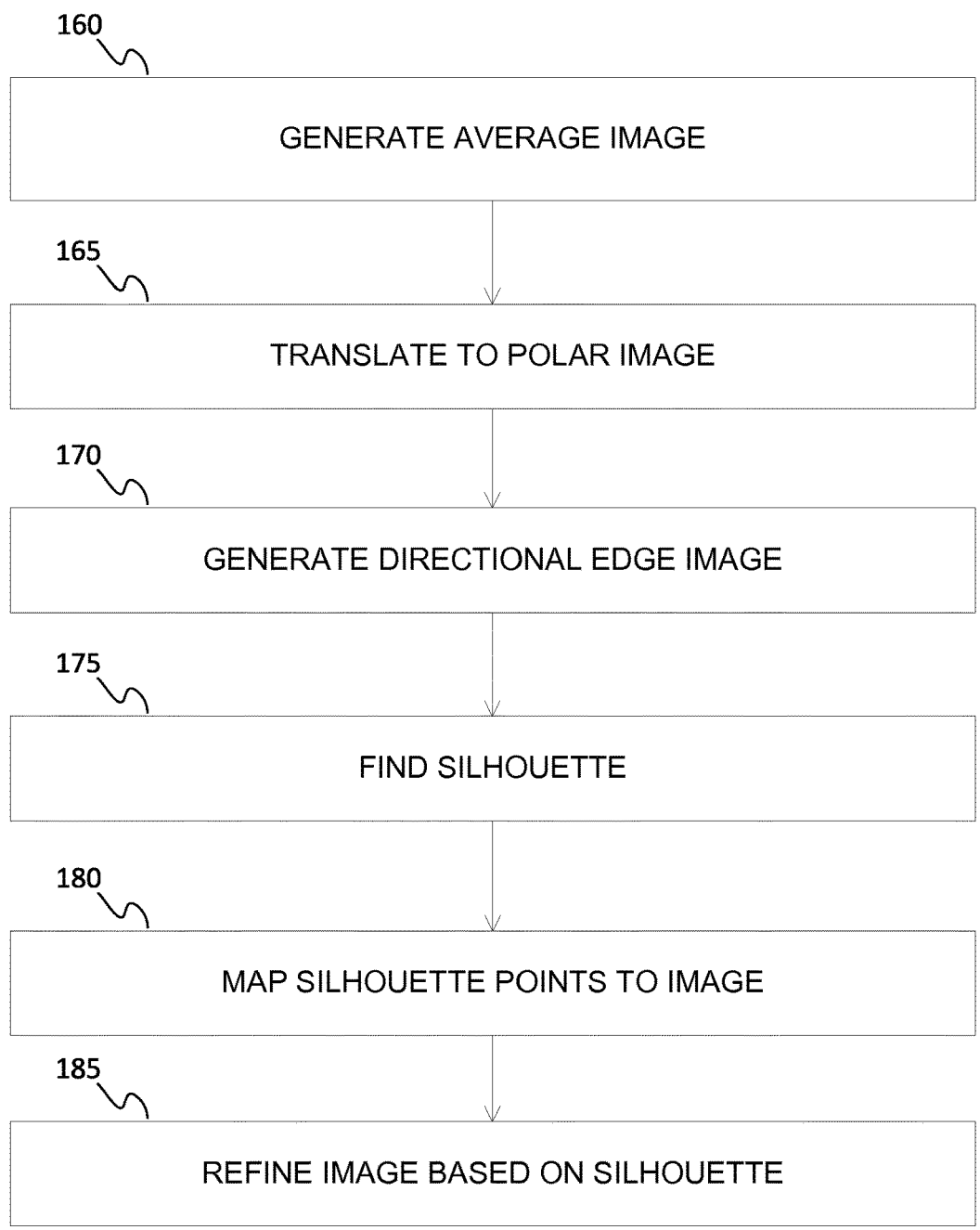
FIG. 2 is a flow chart diagram of one embodiment of a method for processing ultrasound images.

FIG. 2 is a flow chart diagram of an embodiment of image processing, for example the image processing indicated with respect to FIG. 1. The method may be implemented by the system, processor, and/or computer readable media shown in FIG. 4, but other systems may be used. For example, multiple computerized systems may interact and/or communicate to implement the method.

Additional, different, or fewer acts may be performed. For example, act 160 may not be performed. The method is performed in the order shown or another order.

Ultrasonic gel, or other ultrasound conducting coupler, is sometimes detectable in ultrasonic data of a patient, and visible in ultrasound images derived from that data. This gel may cause the outline of patient tissue to be blurred or otherwise occluded, as can be seen by the visible gel 501 in FIG. 5A. These visible traces of the gel in the ultrasound image may be removed from the image during processing.

In act 160, an average image is generated. The average image may be constructed from ultrasound volume data acquired along a coronal plane of a patient, as is shown in FIG. 5B. The average image is formed as a projection along a given direction. The ultrasound volume data may be of a body part, such as a breast, of a patient.

A polar image may be generated in act 165. The polar image is a polar translation of the pixels of the average image, as is shown in FIG. 3C. The pixels may be translated using any technique or transform operable to position the orthogonally referenced elements of the average image into the new polar image using polar coordinate transforms.

In act 170, a directional edge image is generated. A directional edge value is computed for each pixel of the polar image by subtracting the left side of the pixel from the right side of the pixel. To compute the edge of a pixel point, a filter located on the pixel is applied. For example, a [−1 0 1] filter subtracts the left pixel value of the point pixel from the right pixel value of the point. The resulting values will be low because the breast, whose intensity is higher than the other area, is located on the left in the polar image where the directional edge filter with [−1 0 1] is applied to the polar image. The resulting values are low on the border of the breast because the intensity is higher within the breast and lower outside of the breast. An example of such a directional edge image can be see with reference to FIG. 3D.

In act 175, a silhouette is found. The silhouette is the silhouette of the breast. The silhouette may be found by segmenting the polar image using edge values, for example by dividing the edge image into two regions, left for breast and right for non-breast. This segmenting may be achieved by finding the shortest path from the top to the bottom of the polar image, while using the edge values for path weighting. The shortest path is the breast silhouette, such as the path 505 shown in FIG. 5E.

In act 180, the silhouette points are mapped to the original image. This will provide the outline, or silhouette, of the breast tissue in the image. In act 185, the original image is refined based on the silhouette mapping. For example, structure shown in the image outside of the silhouette may be removed to leave a clear outline of the breast tissue.

FIGS. 3A-3D illustrate an embodiment of intervolume anatomical structure detection and/or determination. FIG. 3A shows an acquired ultrasound volume 301 of a patient's breast. The volume is acquired and rendered from a supine anteroposterior (AP) perspective. The volume contains data representing a lesion 302 that exists in the scanned region of the patient's breast. This volume is analyzed, and the lesion 302 is identified. An anatomical landmark or reference, such as the nipple 305, is also identified. The nipple 305 exists as a fixed reference to provide a common landmark throughout acquired volumes of different orientations or views of the breast, such as the AP view, a lateral view (LAT), and/or a medial view (MED). Once the nipple 306 and the lesion 302 are identified, a plane 310 that intersects both is determined.

FIG. 3B shows an image 310 generated from the data of the plane 310. As can be seen from the image 310, both the nipple 306 and the lesions 302 are visible. In this embodiment, the image has been oriented or configured such that the nipple 306 is in the center, or approximate center, of the image 310. The approximate center may be a general center of an image, without being an absolute geometrical center of the image. This may account for nipple 306 or tissue shape variation that may introduce difficulty in determining an absolute center of the image 310. Also, the center of the image may be considered the image lateral center, vertical center, or both.

FIG. 3C shows a second acquired ultrasound volume 311 of the patient's breast. The volume is acquired and rendered from a LAT perspective. The volume 311 also contains data representing the lesion 302 and the nipple 306, as acquired from the LAT perspective. A series of slices 320, 322, 324, 326, 328, 330 are determined and/or generated through the LAT volume. As shown, these slices are oriented incrementally in a radial pattern having the nipple 306 anatomical landmark as the origin. Images are generated of these slices 320, 322, 324, 326, 328, 330.

Figure 3D:
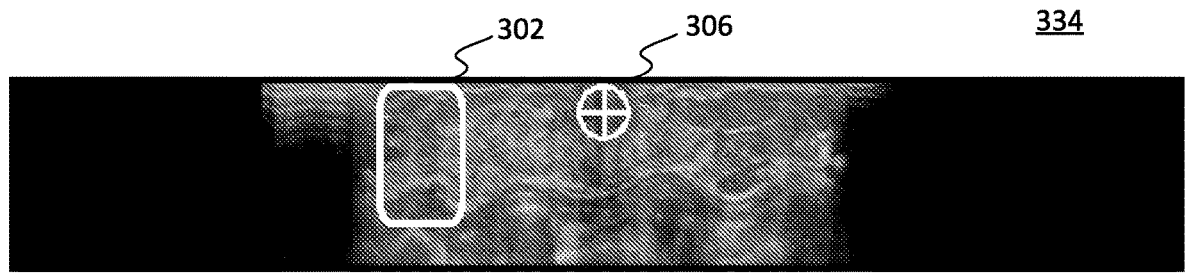

The images generated from the slices 320, 322, 324, 326, 328, 330 are compared to the image 310 generated from the AP perspective volume. FIG. 3D shows the image 334 of the series of images generated from the LAT perspective volume that is determined to be the most similar to the image 310 generated from the AP perspective volume. Image 334 corresponds to a plane 324 of the series of planes. As can be seen in the image, the lesion 302 and the nipple 306 are both represented in the image. The location of the lesion 302 is now identified (automatically, semi-automatically, or manually) and/or determined in the LAT perspective volume, and it is determined that this is a common lesion between both volumes. The lesion as represented in both volumes is linked.

Figure 4:
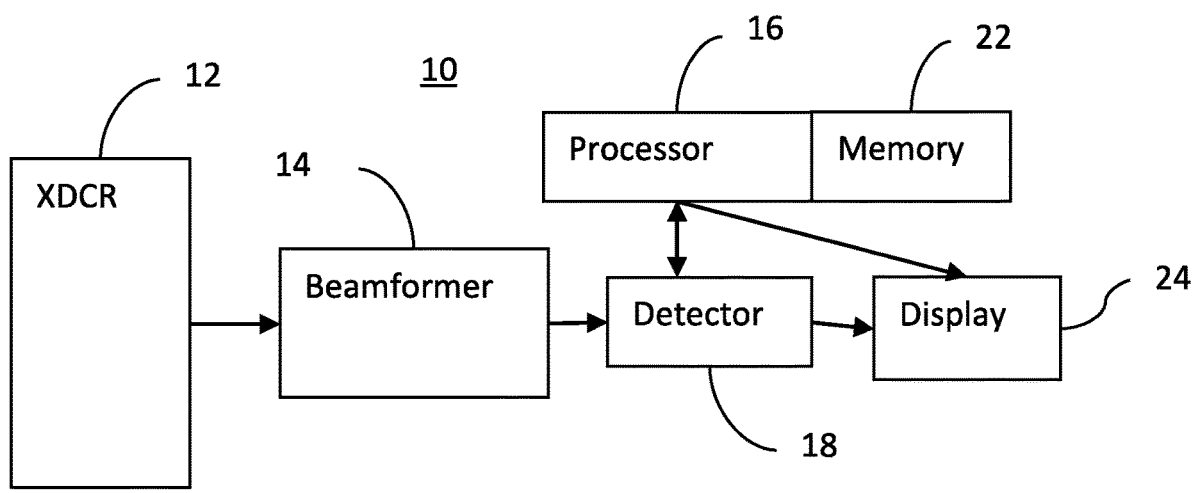
FIG. 4 is a block diagram of one embodiment of an ultrasound system for volume scanning.
Figure 5A:
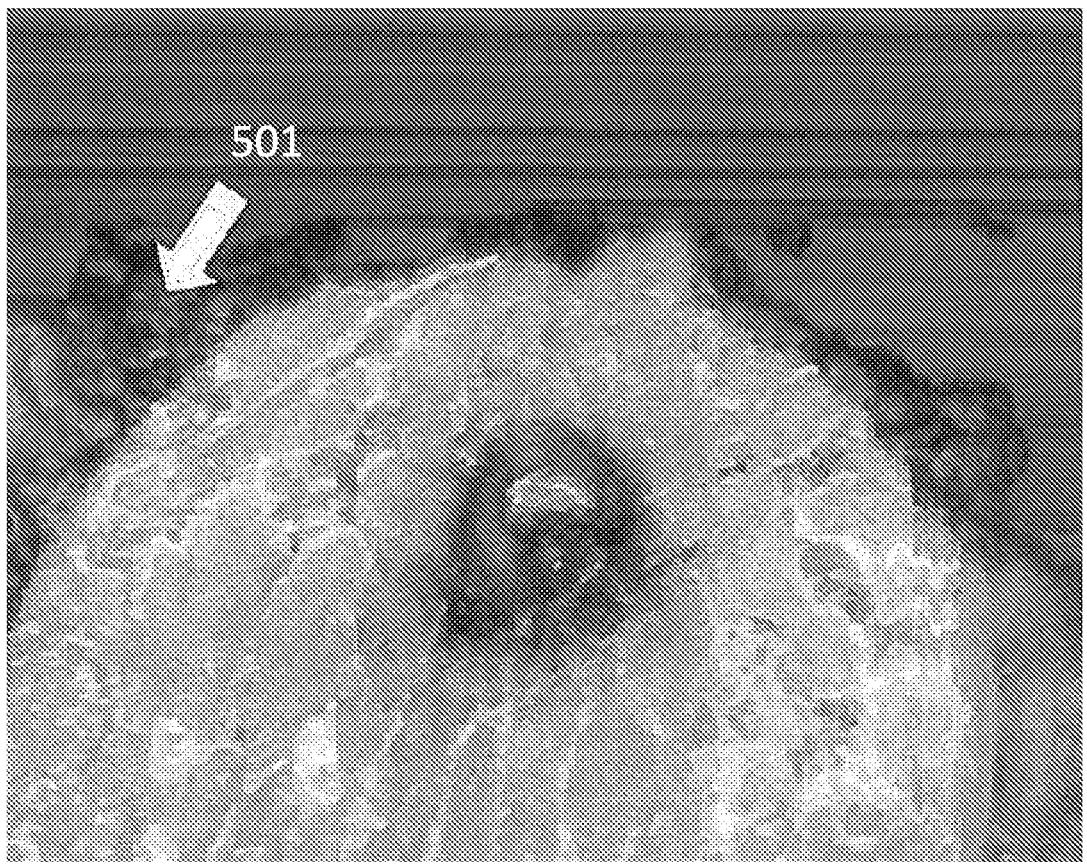

FIG. 4 shows a system 10 for medical diagnostic ultrasound imaging. The system 10 may be used for volume scanning a region of a patient, such as a breast. The system 10 includes a transducer probe 12, a beamformer 14, a processor 16, a detector 18, a memory 22, and a display 24. Additional, different, or fewer components may be provided. For example, the system 10 includes a user interface and/or user input devices. In one embodiment, the system 10 is a medical diagnostic ultrasound imaging system. In other embodiments, the processor 16 and/or memory 22 are part of a workstation or computer different or separate from an ultrasound imaging system. The workstation is adjacent to or remote from the ultrasound imaging system. In some embodiments, the transducer probe 12 incorporates electronics for or is the ultrasound imaging system.

In one embodiment, the system represents an automated breast volume scanner. The transducer probe 12 is provided for scanning the breast. The transducer probe 12 is handheld or may be part of an automated scanning system. For example, the transducer probe 12 is supported by a robotic arm or a support arm. Gravity, servos, motors, springs, hydraulics or other mechanism hold the transducer probe 12 in place against a patient's breast. Other applications than breast imaging may be provided.

The transducer probe 12 is a transducer array for medical diagnostic ultrasound imaging. The transducer probe 12 includes a probe housing and a transducer array. Additional, different, or fewer components may be provided, such as a cable and/or electronics.

The transducer probe 12 includes a planar array, a curved array, a two-dimensional array, a radial array, an annular array, or other multidimensional array of transducer elements. For example, the transducer probe 12 includes a multi- or two-dimensional array. Two-dimensional array has elements spaced in multiple directions (e.g., N×M where both N and M are greater than 1) but does not necessarily have an equal extent in each direction. Multi-dimensional arrays include 1.25D, 1.5D, 1.75D, annular, radial, or other arrangements of elements over an area rather than a line.

In an alternative embodiment, the transducer probe 12 has a one-dimensional array that connects with a guide. The guide is a rail, a pulley, a hydraulic system, a screw drive, mechanical linkage, ball bearings, rack and pinion, or other mechanism for guiding the transducer array in rotational or lateral movement. For example, the guide includes two grooves where the transducer array rests in the grooves and is connected to a pulley or chain. The grooves support the array to move generally perpendicular, such as in an elevation direction. A motor connects with the array, such as through a pulley or gears. The motor applies force to move the transducer array. Any speed of motion may be provided to translate or move the transducer array. The scan head is mechanically translated in the direction parallel to the short axis, causing the transmit plane to sweep across an entire volume. A controller operates the motor at the desired times and/or speed. Any type of motor may be used, such as a stepper motor, electric motor, or pump.

The transducer probe 12 includes a probe housing. For the breast imager, the probe housing is a pod or outer shell of plastic, fiberglass, metal, and/or other material. An acoustic window, such as the flexible bag with or without gel or other ultrasound transmissive substance between the transducer array and the pad, is provided. For example, the pad conforms to the shape of a compressed breast. Gel between the pad and the transducer array allows the adaption and provides an acoustic path from the transducer array to the breast. Alternatively, the probe housing is part of a mammogram system or any other breast compression or scanning system. In an embodiment, such as the embodiment described with respect to FIG. 2, representations of the gel may be removed from an image derived from the ultrasound data.

In alternative embodiments for use scanning the breast or for other uses, the probe housing is for handheld use. The shape and surface texture of the probe housing includes a grip or handle for manual movement of the probe housing. An acoustic window, such as plastic or lens, may be provided.

The probe housing encases, surrounds most of, or is a protective frame work around the transducer array. The probe housing may include handles, grips, latches, connections, a transducer cable, or other components. Electronics may be provided within the probe housing, but the probe housing may be free of active (e.g., transistors, switches, or preamplifiers) electronics.

The acoustic elements of the transducer probe 12 are lead zirconate titanate (PZT) piezoelectric transduction material, ferroelectric relaxor or PVDF materials, capacitive membrane ultrasonic transducer (cMUT) materials, micro-machined membranes or beams, microelectromechanical devices, other piezoelectric material, or other means for acoustic-to-electric and/or electric-to-acoustic transduction. For example, the acoustic elements are cMUT or micromachined structures, such as at least one flexible membrane suspended over a gap with electrodes on each side of the gap for transducing between acoustic and electrical energies. Each acoustic element is formed from one or more, such as 4-8, tens or other numbers of membranes and gaps (i.e., "drums" or cMUT cells). The electrodes of each of the membranes and gaps for a given element are connected in common to form the single acoustic element.

All of the acoustic elements comprise a same type of material, but multiple types of acoustic transducer materials may be used for different acoustic elements. The acoustic elements have one of various possible shapes, such as triangular, rectangular, square, polygonal, hexagonal, circular, irregular, or any combination of shapes on the face of the acoustic element (i.e., portion of the element placed adjacent a volume to be scanned).

The transducer probe 12 converts between electrical signals and acoustic energy for scanning a region of the patient's body. The region of the body scanned is a function of the type of transducer array and position of the transducer probe 12 relative to the patient. A linear aperture may scan a rectangular or square, planar region of the body. As another example, a curved linear aperture may scan a pie shaped region of the body. Scans conforming to other geometrical regions or shapes within the body may be used, such as Vector™ scans. The scans are of a two-dimensional plane, such as scanning at different azimuth angles relative to the aperture. Different planes or different segments of a plane may be scanned by moving the transducer array. To scan a breast volume, the transducer array is also or instead moved mechanically to scan different elevation spaced planes. In other embodiments, a multi-dimensional array is used to electronically steer along elevation and azimuth for a three-dimensional scan of the volume.

The beamformer 14 is configured by hardware and/or software. For example, focus tables are used to determine the delays or phases for steering acoustic beams. Pursuant to software control, the desired waveforms are generated for transmit operation, and the desired receive process is implemented.

In one embodiment, the beamformer 14 includes transmitters or waveform generators for generating electrical waveforms for each element of a transmit aperture. The waveforms are associated with phase and amplitude. The waveforms for a given transmit event may have the same or different phasing. The electrical waveforms are relatively weighted and delayed to form an acoustic beam with a desired phase and amplitude characteristic. For example, the transmit beamformer includes amplifiers, phase rotators, and/or controllers to generate sequential, steered pulses with the desired phase and amplitude in relation to other acoustic beams. Converging, diverging or planar beams may be used.

The beamformer 14 may include receive beamformers, such as delays, phase rotators, amplifiers, and/or adders for relatively delaying and summing received signals to form one or more receive beams with dynamic focusing. For example, using shared processing, separate processing, or combinations thereof, a plurality (e.g., tens or hundreds) of parallel receive beamformers are provided to form a respective plurality of receive beams in response to a given transmit beam. Alternatively, the beamformer 14 includes a processor for Fourier or other analysis of received signals to generate samples representing different spatial locations of the scanned region. In other embodiments, only one or a few (e.g., nine or fewer) receive beams are generated for each transmit beam.

The receive beamformer connects with the receive elements of the transducer array after pre-amplification, any signal conditioning (e.g., filtering) and analog-to-digital conversion. The receive beamformer may be on-chip with the elements.

The transducer probe 12 and beamformer 14 are connected together, such as the transmit beamformer channels connecting through coaxial cables to the transducer probe 12. The transducer probe 12 and beamformer 14 are configured to scan a planar region or a segment of a planar region. The beamformer 14 is controlled or programmed to perform the scan. The beamformer parameters, such as relative delays and/or phasing for focus, apodization, beam amplitude, beam phase, frequency, or others, are set. The aperture for transmit and the aperture for receive on the transducer probe 12 is set. The beamformer 14 and transducer probe 12 are used to generate the waveforms for the aperture and convert the waveforms to acoustic energy for transmitting the beam. The beamformer 14 and transducer probe 12 are used to receive acoustic energy at the receive aperture, convert the acoustic energy to electrical energy, and beamform the received electrical signals.

Electric steering may be used to scan a plane. A volume scan may be performed using mechanical movement of the transducer array or further electric steering. Any pattern or distribution of scan lines and/or apertures may be used. Acoustic energy is transmitted in any of various now known or later developed scan patterns along each scan plane for acquiring data. The scan plane is then altered to another location in the volume by moving the transducer array. By moving the transducer array along the guide, a volume may be scanned. The volume is represented by data for a plurality of planes.

For each plane position, the beamformer is configured to scan the plane once. Alternatively, the plane is scanned multiple times but with different scan line angles in azimuth for compounding spatially. Different aperture locations may be used for scanning a given location from different angles.

For a given volume, the scans may be repeated. By repeating the scans, a sequence of frames of voxel data is obtained. Each frame represents the entire three-dimensional scanned volume, but may only represent smaller regions within the volume, such as a plane. By repeating the scanning, a plurality of frames of beamformed data representing the volume and/or plane is acquired. Any of scan line, part of frame, frame, or group of frame interleaving may be used.

The detector 18 is configured to detect data output by the beamformer 14 and responsive to the transducer array. The detector 18 is an ultrasound detector. The detector is configured by hardware and/or software to detect from the beamformed and/or interpolated data. Any detection may be used, such as B-mode, Doppler or color flow mode, harmonic mode, or other now known or later developed modes. B-mode and some harmonic modes use single pulse scan techniques for detection. The intensity of the received signals in the frequency band of interest is calculated. Multiple pulse techniques, such as flow mode estimation of velocity or energy, may be used.

The detector 18 detects the response to the transmit beams for the scan of the volume. The spatial and/or temporal resolution of the detected data is based on the beamforming or scanning resolution. Detected data representing the volume is provided.

The processor 16 is a rendering processor configured by hardware and/or software. The processor 16 is a general processor, control processor, application-specific integrated circuit, field-programmable gate array, graphics processing unit, digital circuit, analog circuit, digital signal processor, combinations thereof, or other now known or later developed device for generating a three-dimensional rendering of a volume scanned with different planes. The processor 16 is a single device or group of devices. For example, the processor 16 includes separate processors operating in parallel or sequence. As another example, the processor 16 includes a network of devices for distributed processing in parallel or sequence. In one embodiment, the processor 16 is a specific device for three-dimensional image rendering, such as a graphics processing unit, graphics card, or other device for rendering.

The processor 16 uses surface rendering, projection rendering, alpha blending, texturing, or other now known or later developed rendering. The data may be resampled to a regular voxel grid. Alternatively, the rendering is performed from data in a scan format, such as associated with the actual scan lines and/or interpolated scan lines. In yet other embodiments, the processor 16 is not provided or is a scan converter for generating a two-dimensional image representing a scanned plane or a reconstruction of a plane from a scanned volume.

The processor 16, the detector 18, or a separate processor generates images from the volume scan and/or plane scan or other data output from the detector 18. For example, grayscale and/or color coding is used to generate a B-mode, Doppler mode, or B-mode Doppler mode combination. Any image, such as a three-dimensional rendering, is output to the display 24.

In an embodiment, the processor 16 is configured to detect the anatomical structure in a second volume of ultrasound data. The processor 16 may also be configured to generate a second image of a second slice of the second volume where the second slice defines data representing a plane in the second volume and includes the anatomical structure and an anatomical landmark. The processor 16 may also be configured to generate a series of images of slices of the first volume where the slices of the first volume define data representing planes in the first volume and including the anatomical landmark. The processor 16 may also be configured to compare the series of images to the second image, and identify, based on the comparison, a first image from the series of images that contains a representation of the anatomical structure.

The display 24 is a CRT, LCD, plasma, projector, printer, or other now known or later display device. The display 24 receives the image data from the processor 16 or other component and generates the image. A three-dimensional rendering, two-dimensional image, or other image is displayed.

The memory 22 is a tangible (non-transitory) computer readable storage medium, such as a cache, buffer, register, RAM, removable media, hard drive, optical storage device, or other computer readable storage media. The memory 22 is tangible by not being a signal, but a device. Computer readable storage media include various types of volatile and nonvolatile storage media. The memory 22 is accessible by the processor 16.

The memory 22 stores data representing instructions executable by the programmed processor 16, processor of the beamformer 14, and/or other processor for scanning with ultrasound, generating images, comparing, identifying, and/or linking. The instructions for implementing the processes, methods and/or techniques discussed herein are provided on computer-readable storage media or memories. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

In an embodiment, the memory 22 is a non-transitory computer readable storage medium having stored therein data representing instructions executable by a programmed processor for detecting an anatomical structure in a first volume of ultrasound data. The instructions may be operable and/or otherwise configured to cause the system 10 to detect the anatomical structure in a second volume of ultrasound data, the second volume and the first volume representing different but overlapping regions of a patient. The instructions may also be operable and/or otherwise configured to cause the system 10 to generate a second image of a second slice of the second volume, the second slice comprising data representing a plane in the second volume and including the anatomical structure and an anatomical landmark. The instructions may also be operable and/or otherwise configured to cause the system 10 to generate a series of images of slices of the first volume, the slices of the first volume comprising data representing planes in the first volume and including the anatomical landmark. The instructions may also be operable and/or otherwise configured to cause the system 10 to compare the series of images to the second image, and identify based on the comparing, a first image from the series of images that contains a representation of the anatomical structure.

While the invention has been described above by reference to various embodiments, it should be understood that many changes and modifications can be made without departing from the scope of the invention. The above embodiments are examples. It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method of detecting an anatomical structure in a first volume of ultrasound data, the method comprising:
    scanning the patient by an ultrasound volume scanner, the scanning providing a second volume of ultrasound data;
    detecting the anatomical structure in the second volume of ultrasound data, the second volume and the first volume representing different but overlapping regions of a patient;
    generating, by a processor, a second image of a second slice of the second volume, the second slice comprising data representing a plane in the second volume and including the anatomical structure and an anatomical landmark;
    generating, by the processor, a series of images of slices of the first volume, the slices of the first volume comprising data representing planes in the first volume and including the anatomical landmark;
    comparing, by the processor, the series of images to the second image;
    identifying, by the processor based on the comparing, a first image from the series of images that contains a representation of the anatomical structure; and
    presenting the first image and the second image on a display.

2. The method of claim 1, further comprising:
    linking, in a database, the first image and the second image with the anatomical structure.

3. The method of claim 1, wherein the overlapping regions of the patient comprise a breast of the patient.

4. The method of claim 3, wherein the anatomical structure is a lesion in the breast of the patient.

5. The method of claim 3, wherein the anatomical landmark is a nipple of the breast of the patient.

6. The method of claim 1, wherein the detecting the anatomical structure in the second volume comprises manually indicating the location of the anatomical structure by a user with an input device.

7. The method of claim 1, wherein the detecting the anatomical structure in the second volume comprises automatically detecting the anatomical structure using edge detection.

8. The method of claim 1, wherein the generating the series of images of slices of the first volume comprises generating images for slices of the first volume incrementally in a radial pattern having the anatomical landmark as the origin.

9. The method of claim 8, wherein the radial pattern includes slices of the first volume selected for a pre-determined range of angles.

10. The method of claim 1, wherein the generating the second image and the generating the series of images comprises generating the images with the anatomical landmark in a center of the images.

11. The method of claim 1, further comprising after the generating the second image and the generating the series of images:
    establishing an outline of a body part of the patient in the second image and the series of images; and
    removing ultrasound representations of non-tissue matter outside the outline in the second image and the series of images.

12. The method of claim 11, wherein the comparing the series of images to the second image comprises comparing the second image and the series of images after the removing.

13. The method of claim 1, wherein the comparing comprises the generation of a similarity value between the images of the series of images and the second image.

14. The method of claim 13, wherein the identifying comprises identifying the first image as having a largest similarity value of the series of images.

15. A system for detecting an anatomical structure in a first volume of ultrasound data, the system comprising:
    an ultrasound scanner configured to scan a patient, the scan providing a second volume of ultrasound data;
    at least one memory operable to store the first volume of ultrasound data and the second volume of ultrasound data, the ultrasound data of the first and second volumes representing different but overlapping regions of a patient;
    a processor configured to:
    detect the anatomical structure in the second volume of ultrasound data;
    generate a second image of a second slice of the second volume of the ultrasound data, the second slice comprising data representing a plane in the second volume and including the anatomical structure and an anatomical landmark;
    generate a series of images of slices of the first volume, the slices of the first volume comprising data representing planes in the first volume and including the anatomical landmark;
    compare the series of images to the second image; and
    identify, based on the comparison, a first image from the series of images that contains a representation of the anatomical structure; and
    a display configured to present the first and second images.

16. The system of claim 15, wherein the processor is further configured to generate an association in a database of the first image and the second image with the anatomical structure.

17. The system of claim 15, wherein the overlapping regions of the patient comprise a breast of the patient, and the anatomical structure is a lesion in the breast of the patient.

18. A non-transitory computer readable storage medium having stored therein data representing instructions executable by a programmed processor for detecting an anatomical structure in a first volume of ultrasound data, the storage medium comprising instructions to:
    scan a patient with ultrasound, the scan resulting in a second volume of ultrasound data;
    detect the anatomical structure in the second volume of ultrasound data, the second volume and the first volume representing different but overlapping regions of a patient;
    generate a second image of a second slice of the second volume, the second slice comprising data representing a plane in the second volume and including the anatomical structure and an anatomical landmark;
    generate a series of images of slices of the first volume, the slices of the first volume comprising data representing planes in the first volume and including the anatomical landmark;
    compare the series of images to the second image;
    identify based on the comparing, a first image from the series of images that contains a representation of the anatomical structure; and
    present the first image and the second image on a display.

* * * * *